US005527894A

United States Patent [19]
Gold et al.

[11] Patent Number: 5,527,894
[45] Date of Patent: Jun. 18, 1996

[54] LIGANDS OF HIV-1 TAT PROTEIN

[75] Inventors: Larry M. Gold; Craig Tuerk, both of Boulder, Colo.

[73] Assignee: NeXstar Pharmacueticals, Inc., Boulder, Colo.

[21] Appl. No.: 243,870

[22] Filed: May 17, 1994

Related U.S. Application Data

[63] Continuation of Ser. No. 953,694, Sep. 29, 1992, which is a continuation-in-part of Ser. No. 714,131, Jun. 10, 1991, Pat. No. 5,475,096, which is a continuation-in-part of Ser. No. 536,428, Jun. 11, 1990, abandoned.

[51] Int. Cl.[6] .......................... C07H 21/02; C07H 21/04; C12Q 1/68
[52] U.S. Cl. ................................. 536/22.1; 435/6
[58] Field of Search ....................... 435/6, 91.2; 536/22.1

[56] References Cited

U.S. PATENT DOCUMENTS

| | | | |
|---|---|---|---|
| 4,910,132 | 3/1990 | Knight et al. | 435/5 |
| 5,270,163 | 12/1993 | Gold et al. | 435/6 |

FOREIGN PATENT DOCUMENTS

| | | |
|---|---|---|
| 2183661 | 6/1987 | United Kingdom . |
| WO89/06694 | 7/1989 | WIPO . |

OTHER PUBLICATIONS

Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Tuerk & Gold, Science 249:505–510 (3 Aug. 1990).
Kinzler et al., "Whole genome PCR: application to the identification of sequences . . . ", Nuc. Acids Res. 17(10):3645–3653 (1989).

*Primary Examiner*—Stephanie W. Zitomer
*Attorney, Agent, or Firm*—Swanson & Bratschun

[57] ABSTRACT

Methods are described for the production of nucleic acid ligands to the HIV-1 tat protein. Motifs I, II and III in FIG. 3 are nucleic acid ligands identified by the disclosed methods.

6 Claims, 6 Drawing Sheets

TAR RNA

Tat Ligand Sequences

| Isolate Number | Sequence |
|---|---|
| 4, 12, 16 | aaGCCUCAGUAAGGCAACGGAAUCCGCA———AGAGGAUGGACCACuucgacaug |
| 7, 9 | gcucaaCACGGAAAGGAGGGAAUCUU—GAAGAACCCGGACCACuucgacaug |
| 5 | cucaaGCGGAAAUGGAAACGGAGCCAUCAAC——AAGCUGGGGACCACAuucgacau |
| 26 | ucaaCAAAACGAAGGAUGACCCAA———GCAGGUCAGGACCACuucgacaug |
| 19 | cgucaaACGAAGGAAACGGAUGCGGACAUAUGUGCCGCAGGACCACuucgacaug |
| 21 | aaACACAUCGAAGGUAACGGAGCGAAAAA———GAACGCGGACCACuucgacaug |
| 30 | aacgcucaaGCGGGCAACGGAGUCCUGA———ACGGACGGACCACGCAAGAAu |

Tat ligand motif I

FIG. 2A

```
                                                                    ⌐III
                                                                   aaGAGAAUCUAACGAGACGUAAGCCGUCGGAGAAUGAGACGAuucgacaugaggc
                              15
                              14,25,28    aGUGGAGGACUAAAUGAGAGGCGUAACGA——CCGGAGAUUGAGACGUCuucgacaugagg
                              31,33
                              17          cgcucaaGGGCGACGGGACUGCAAGCAUGGAGCUAACGAGAAAAUUGCuucgaca
                               1          cgcucaaCCUGGAGAGGAUCGCUCGGGCCUUGAUCCCCAGAUCAAAuucgaca
```

FIG. 2C

Tat motif I

Tat motif II

Tat motif III

LIGANDS OF HIV-1 TAT PROTEIN

This is a continuation of application Ser. No. 07/953,694 filed on Sep. 29, 1992 which is a continuation-in-part of Ser. No. 07/714,131 filed Jun. 10, 1991, now U.S. Pat. No. 5,475,096, issued Dec. 12, 1995, entitled Nucleic Acid Ligands and U.S. patent application Ser. No. 07/536,428, filed Jun. 11, 1990, entitled Systematic Evolution of Ligands by Exponential Enrichment, now abandoned.

FIELD OF THE INVENTION

Described herein are methods for identifying and preparing ligands to a HIV-1 protein critical in the reproduction of the HIV-1 virus. Also included are the specific ligands identified pursuant to such methods. Specifically, nucleic acid ligands are described to the HIV-1 tat protein. The method utilized herein for identifying such nucleic acid ligands is called SELEX, an acronym for Systematic Evolution of Ligands for EXponential enrichment. Also included within the scope of this invention are modified nucleic acid ligands and mimetic ligands that are informed by the nucleic acid ligands identified herein.

BACKGROUND OF THE INVENTION

Most proteins or small molecules are not known to specifically bind to nucleic acids. The known protein exceptions are those regulatory proteins such as repressors, polymerases, activators and the like which function in a living cell to bring about the transfer of genetic information encoded in the nucleic acids into cellular structures and the replication of the genetic material. Furthermore, small molecules such as GTP bind to some intron RNAs.

Living matter has evolved to limit the function of nucleic acids to a largely informational role. The Central Dogma, as postulated by Crick, both originally and in expanded form, proposes that nucleic acids (either RNA or DNA) can serve as templates for the synthesis of other nucleic acids through replicative processes that "read" the information in a template nucleic acid and thus yield complementary nucleic acids. All of the experimental paradigms for genetics and gene expression depend on these properties of nucleic acids: in essence, double-stranded nucleic acids are informationally redundant because of the chemical concept of base pairs and because replicative processes are able to use that base pairing in a relatively error-free manner.

The individual components of proteins, the twenty natural amino acids, possess sufficient chemical differences and activities to provide an enormous breadth of activities for both binding and catalysis. Nucleic acids, however, are thought to have narrower chemical possibilities than proteins, but to have an informational role that allows genetic information to be passed from virus to virus, cell to cell, and organism to organism. In this context nucleic acid components, the nucleotides, must possess only pairs of surfaces that allow informational redundancy within a Watson-Crick base pair. Nucleic acid components need not possess chemical differences and activities sufficient for either a wide range of binding or catalysis.

However, some nucleic acids found in nature do participate in binding to certain target molecules and even a few instances of catalysis have been reported. The range of activities of this kind is narrow compared to proteins and more specifically antibodies. For example, where nucleic acids are known to bind to some protein targets with high affinity and specificity, the binding depends on the exact sequences of nucleotides that comprise the DNA or RNA ligand. Thus, short double-stranded DNA sequences are known to bind to target proteins that repress or activate transcription in both prokaryotes and eukaryotes. Other short double-stranded DNA sequences are known to bind to restriction endonucleases, protein targets that can be selected with high affinity and specificity. Other short DNA sequences serve as centromeres and telomeres on chromosomes, presumably by creating ligands for the binding of specific proteins that participate in chromosome mechanics. Thus, double-stranded DNA has a well-known capacity to bind within the nooks and crannies of target proteins whose functions are directed to DNA binding. Single-stranded DNA can also bind to some proteins with high affinity and specificity, although the number of examples is rather smaller. From the known examples of double-stranded DNA binding proteins, it has become possible to describe some of the binding interactions as involving various protein motifs projecting amino acid side chains into the major groove of B form double-stranded DNA, providing the sequence inspection that allows specificity.

Double-stranded RNA occasionally serves as a ligand for certain proteins, for example, the endonuclease RNase III from *E. coli*. There are more known instances of target proteins that bind to single-stranded RNA ligands, although in these cases the single-stranded RNA often forms a complex three-dimensional shape that includes local regions of intramolecular double-strandedness. The amino-acyl tRNA synthetases bind tightly to tRNA molecules with high specificity. A short region within the genomes of RNA viruses binds tightly and with high specificity to the viral coat proteins. A short sequence of RNA binds to the bacteriophage T4-encoded DNA polymerase, again with high affinity and specificity. Thus, it is possible to find RNA and DNA ligands, either double- or single-stranded, serving as binding partners for specific protein targets. Most known DNA binding proteins bind specifically to double-stranded DNA, while most RNA binding proteins recognize single-stranded RNA. This statistical bias in the literature no doubt reflects the present biosphere's statistical predisposition to use DNA as a double-stranded genome and RNA as a single-stranded entity in the roles RNA plays beyond serving as a genome. Chemically there is no strong reason to dismiss single-stranded DNA as a fully able partner for specific protein interactions.

RNA and DNA have also been found to bind to smaller target molecules. Double-stranded DNA binds to various antibiotics, such as actinomycin D. A specific single-stranded RNA binds to the antibiotic thiostreptone; specific RNA sequences and structures probably bind to certain other antibiotics, especially those whose functions is to inactivate ribosomes in a target organism. A family of evolutionary related RNAs binds with specificity and decent affinity to nucleotides and nucleosides (Bass, B. and Cech, T. (1984) Nature 308:820–826) as well as to one of the twenty amino acids (Yarus, M. (1988) Science 240:1751–1758). Catalytic RNAs are now known as well, although these molecules perform over a narrow range of chemical possibilities, which are thus far related largely to phosphodiester transfer reactions and hydrolysis of nucleic acids.

Despite these known instances, the great majority of proteins and other cellular components are thought not to bind to nucleic acids under physiological conditions and such binding as may be observed is non-specific. Either the capacity of nucleic acids to bind other compounds is limited to the relatively few instances enumerated supra, or the chemical repertoire of the nucleic acids for specific binding is avoided (selected against) in the structures that occur naturally. The present invention is premised on the inventors' fundamental insight that nucleic acids as chemical compounds can form a virtually limitless array of shapes, sizes and configurations, and are capable of a far broader repertoire of binding and catalytic functions than those displayed in biological systems.

The chemical interactions have been explored in cases of certain known instances of protein-nucleic acid binding. For example, the size and sequence of the RNA site of bacteriophage R17 coat protein binding has been identified by Uhlenbeck and coworkers. The minimal natural RNA binding site (21 bases long) for the R17 coat protein was determined by subjecting variable-sized labeled fragments of the mRNA to nitrocellulose filter binding assays in which protein-RNA fragment complexes remain bound to the filter (Carey et al. (1983) Biochemistry 22:2601). A number of sequence variants of the minimal R17 coat protein binding site were created in vitro in order to determine the contributions of individual nucleic acids to protein binding (Uhlenbeck et al. (1983) J. Biomol. Structure Dynamics 1:539 and Romaniuk et al. (1987) Biochemistry 26:1563). It was found that the maintenance of the hairpin loop structure of the binding site was essential for protein binding but, in addition, that nucleotide substitutions at most of the single-stranded residues in the binding site, including a bulged nucleotide in the hairpin stem, significantly affected binding. In similar studies, the binding of bacteriophage Qβ coat protein to its translational operator was examined (Witherell and Uhlenbeck (1989) Biochemistry 28:71). The Qβ coat protein RNA binding site was found to be similar to that of R17 in size, and in predicted secondary structure, in that it comprised about 20 bases with an 8 base pair hairpin structure which included a bulged nucleotide and a 3 base loop. In contrast to the R17 coat protein binding site, only one of the single-stranded residues of the loop is essential for binding and the presence of the bulged nucleotide is not required. The protein-RNA binding interactions involved in translational regulation display significant specificity.

Nucleic acids are known to form secondary and tertiary structures in solution. The double-stranded forms of DNA include the so-called B double-helical form, Z-DNA and superhelical twists (Rich, A. et al. (1984) Ann. Rev. Biochem. 53:791–846). Single-stranded RNA forms localized regions of secondary structure such as hairpin loops and pseudoknot structures (Schimmel, P. (1989) Cell 58:9–12). However, little is known concerning the effects of unpaired loop nucleotides on stability of loop structure, kinetics of formation and denaturation, thermodynamics, and almost nothing is known of tertiary structures and three dimensional shape, nor of the kinetics and thermodynamics of tertiary folding in nucleic acids (Tuerk, C. et al. (1988) Proc. Natl. Acad. Sci. USA 85:1364–1368).

A type of in vitro evolution was reported in replication of the RNA bacteriophage Qβ. Mills, D. R. et al. (1967) Proc. Natl. Acad. Sci USA 58:217–224; Levinsohn, R. and Spiegleman, S. (1968) Proc. Natl. Acad. Sci. USA 60:866–872; Levinsohn, R. and Spiegleman S. (1969) Proc. Natl. Acad. Sci. USA 63:805–811; Saffhill, R. et al. (1970) J. Mol. Biol. 51:531–539; Kacian, D. L. et al. (1972) Proc. Natl. Acad. Sci. USA 69:3038–3042; Mills, D. R. et al. (1973) Science 180:916–927. The phage RNA serves as a poly-cistronic messenger RNA directing translation of phage-specific proteins and also as a template for its own replication catalyzed by Qβ RNA replicase. This RNA replicase was shown to be highly specific for its own RNA templates. During the course of cycles of replication in vitro small variant RNAs were isolated which were also replicated by Qβ replicase. Minor alterations in the conditions under which cycles of replication were performed were found to result in the accumulation of different RNAs, presumably because their replication was favored under the altered conditions. In these experiments, the selected RNA had to be bound efficiently by the replicase to initiate replication and had to serve as a kinetically favored template during elongation of RNA. Kramer et al. (1974) J. Mol. Biol. 89:719 reported the isolation of a mutant RNA template of Qβ replicase, the replication of which was more resistant to inhibition by ethidium bromide than the natural template. It was suggested that this mutant was not present in the initial RNA population but was generated by sequential mutation during cycles of in vitro replication with Qβ replicase. The only source of variation during selection was the intrinsic error rate during elongation by Qβ replicase. In these studies what was termed "selection" occurred by preferential amplification of one or more of a limited number of spontaneous variants of an initially homogenous RNA sequence. There was no selection of a desired result, only that which was intrinsic to the mode of action of Qβ replicase.

Joyce and Robertson (Joyce (1989) in *RNA: Catalysis, Splicing, Evolution,* Belfort and Shub (eds.), Elsevier, Amsterdam pp. 83–87; and Robertson and Joyce (1990) Nature 344:467) reported a method for identifying RNAs which specifically cleave single-stranded DNA. The selection for catalytic activity was based on the ability of the ribozyme to catalyze the cleavage of a substrate ssRNA or DNA at a specific position and transfer the 3'-end of the substrate to the 3'-end of the ribozyme. The product of the desired reaction was selected by using an oligodeoxynucleotide primer which could bind only to the completed product across the junction formed by the catalytic reaction and allowed selective reverse transcription of the ribozyme sequence. The selected catalytic sequences were amplified by attachment of the promoter of T7 RNA polymerase to the 3'-end of the cDNA, followed by transcription to RNA. The method was employed to identify from a small number of ribozyme variants the variant that was most reactive for cleavage of a selected substrate.

The prior art has not taught or suggested more than a limited range of chemical functions for nucleic acids in their interactions with other substances: as targets for proteins that had evolved to bind certain specific oligonucleotide sequences; and more recently, as catalysts with a limited range of activities. Prior "selection" experiments have been limited to a narrow range of variants of a previously described function. Now, for the first time, it will be understood that the nucleic acids are capable of a vastly broad range of functions and the methodology for realizing that capability is disclosed herein.

U.S. patent application Ser. No. 07/536,428 filed Jun. 11, 1990, of Gold and Tuerk, entitled Systematic Evolution of Ligands by Exponential Enrichment, and U.S. Pat. No. 5,475,096 issued Dec. 12, 1995 of Gold and Tuerk, entitled Nucleic Acid Ligands (See also WO 91/19813) describe a fundamentally novel method for making a nucleic acid ligand for any desired target. Each of these applications, collectively referred to herein as the SELEX Patent Applications, is specifically incorporated herein by reference.

The method of the SELEX Patent Applications is based on the unique insight that nucleic acids have sufficient capacity for forming a variety of two- and three-dimensional structures and sufficient chemical versatility available within their monomers to act as ligands (form specific binding pairs) with virtually any chemical compound, whether large or small in size.

The method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the method, termed SELEX herein, includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

While not bound by a theory of preparation, SELEX is based on the inventors' insight that within a nucleic acid mixture containing a large number of possible sequences and structures there is a wide range of binding affinities for a given target. A nucleic acid mixture comprising, for example a 20 nucleotide randomized segment can have $4^{20}$ candidate possibilities. Those which have the higher affinity constants for the target are most likely to bind. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

In one embodiment of the method of the SELEX Patent Applications, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX until a single nucleic acid ligand is identified. The target-specific nucleic acid ligand solution may include a family of nucleic acid structures or motifs that have a number of conserved sequences and a number of sequences which can be substituted or added without significantly effecting the affinity of the nucleic acid ligands to the target. By terminating the SELEX process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, psuedoknots and myriad combinations of the same. Almost all known cases of such motifs suggest that they can be formed in a nucleic acid sequence of no more than 30 nucleotides. For this reason, it is often preferred that SELEX procedures with contiguous randomized segments be initiated with nucleic acid sequences containing a randomized segment of between about 20-50 nucleotides.

The SELEX Patent Applications also describe methods for obtaining nucleic acid ligands that bind to more than one site on the target molecule, and to nucleic acid ligands that include non-nucleic acid species that bind to specific sites on the target. The SELEX method provides means for isolating and identifying nucleic acid ligands which bind to any envisonable target. However, in preferred embodiments the SELEX method is applied to situations where the target is a protein, including both nucleic acid-binding proteins and proteins not known to bind nucleic acids as part of their biological function.

The HIV-1 tat protein activates transcription in the long terminal repeat (LTR) of the viral genome of HIV-1. See, Cullen et al. (1989) Cell 58:423–426. The mechanism of activation is unclear or at least controversial, but requires that the transcribed RNA contain a specific hairpin structure with a trinucleotide bulge (called TAR). The natural TAR RNA and the site of tat interaction is shown in FIG. 1. A small basic domain of the tat protein has been shown to interact directly with the TAR RNA sequence. See, Weeks et al. (1990) Science 249:1281–1285; Roy et al. (1990) Genes Dev. 4:1365–1373; Calnan et al. (1991a) Genes Dev. 5:201–210. Arginines within this basic domain are apparently crucial to the interaction. See, Calnan et al. (1991a) supra; Subramanian et al. (1991) EMBO 10:2311–2318; Calnan et al (1991b) Science 252:1167–1171. Arginine alone is specifically bound by the TAR RNA sequence and may compete for tat protein binding. See, Tao et al. (1992) Proc. Natl. Acad. Sci. USA 89:2723–2726; Puglisi et al. (1992) Science 257:76–80.

Tat—TAR interactions alone are insufficient to support transactivation; presumably a cellular factor —a 68 kD loop binding protein—is required for cooperative binding with the tat protein to TAR, and subsequent in vivo or in vitro transactivation. See, Marciniak et al. (1990a) Proc. Natl. Acad. Sci. USA 87:3624–3628; Marciniak et al. (1990b) Cell 63:791–802. Overexpression of the TAR sequence in retrovirally transformed cell lines renders them highly resistant to HIV-1 infections. See, Sullenger et al. (1990) Cell 63:601–608.

SUMMARY OF THE INVENTION

The present invention includes methods for identifying and producing nucleic acid ligands and the nucleic acid ligands so identified and produced.

Nucleic acid sequences are provided that are ligands to the HIV-1 tat protein. More specifically, RNA sequences have been identified that are capable of binding to the tat protein. Included within the invention are the nucleic acid ligand solutions shown in FIGS. 2 and 3.

Further included in this invention is a method of identifying nucleic acid ligands and ligand solutions to the HIV-1 tat protein comprising the steps of a) preparing a candidate mixture of nucleic acids; b) partitioning between members of said candidate mixture on the basis of affinity to the tat protein; and c) amplifying the selected molecules to yield a mixture of nucleic acids enriched for nucleic acid sequences with a relatively higher affinity for binding to the tat protein.

The present invention also includes modified nucleotide sequences based on the nucleic acid ligand solutions identified herein and mixtures of the same.

DETAILED DESCRIPTION OF THE PREFERRED EMBODIMENTS

Figure 1:
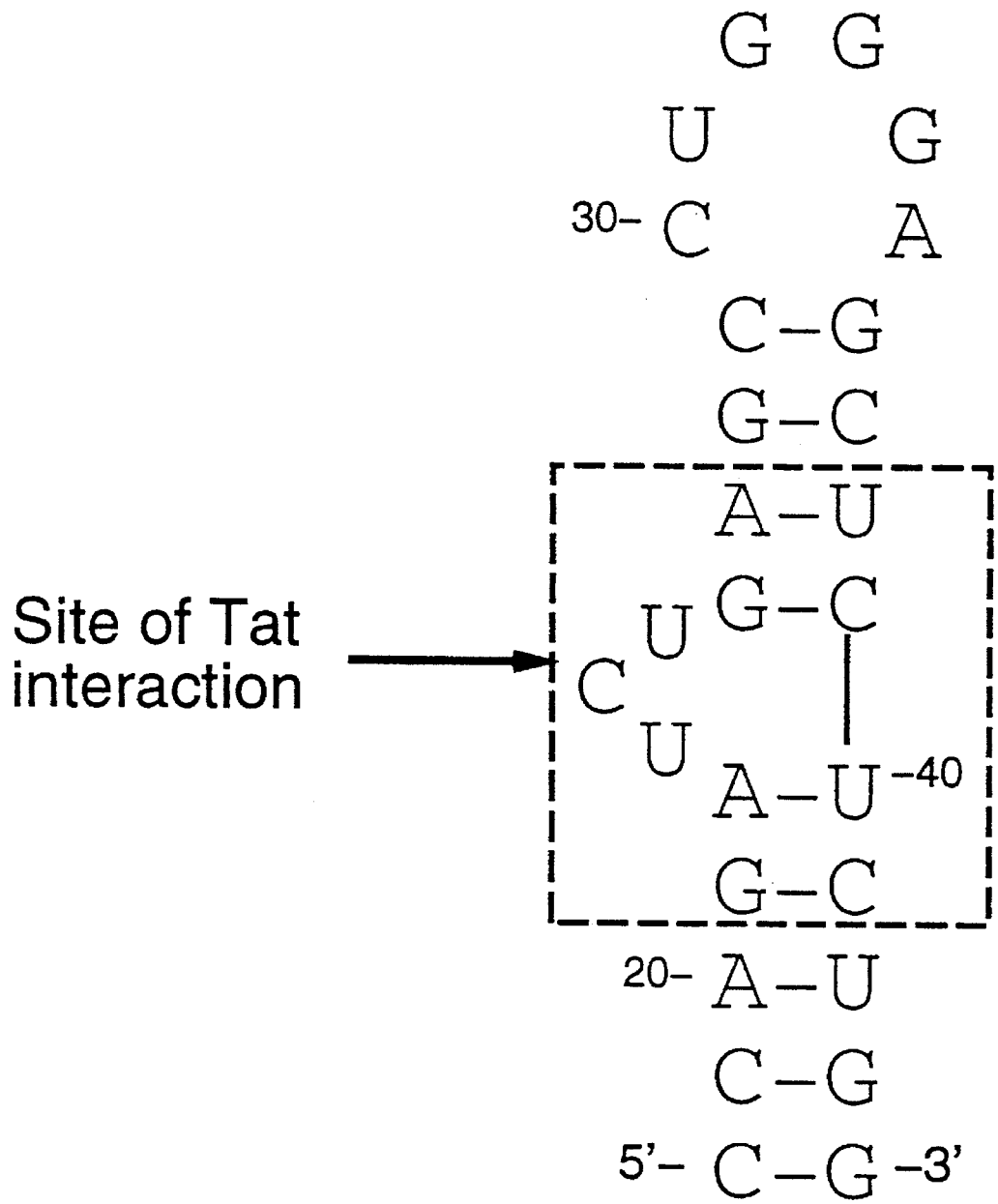
FIG. 1 depicts the natural RNA sequence (SEQ ID NO:20) (or TAR RNA) from HIV-1 with which the tat protein interacts. The boxed region of the sequence identifies those nucleotides that have been found to be important in the tat-TAR interaction.

This application is an extension and an application of the method for identifying nucleic acid ligands referred to as SELEX. The SELEX method is described in detail in U.S. Pat. No. 5,475,096 issued Dec. 12, 1995 entitled Nucleic Acid Ligan, continuation-in-part of application Ser. No. 07/536,428 filed Jun. 11, 1990 entitled Systematic Evolution of Ligands by EXponential Enrichments, now abandoned. The full text of these applications, including but not limited to, all definitions and descriptions of the SELEX process, are specifically incorporated herein by reference.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

Figure 2B:
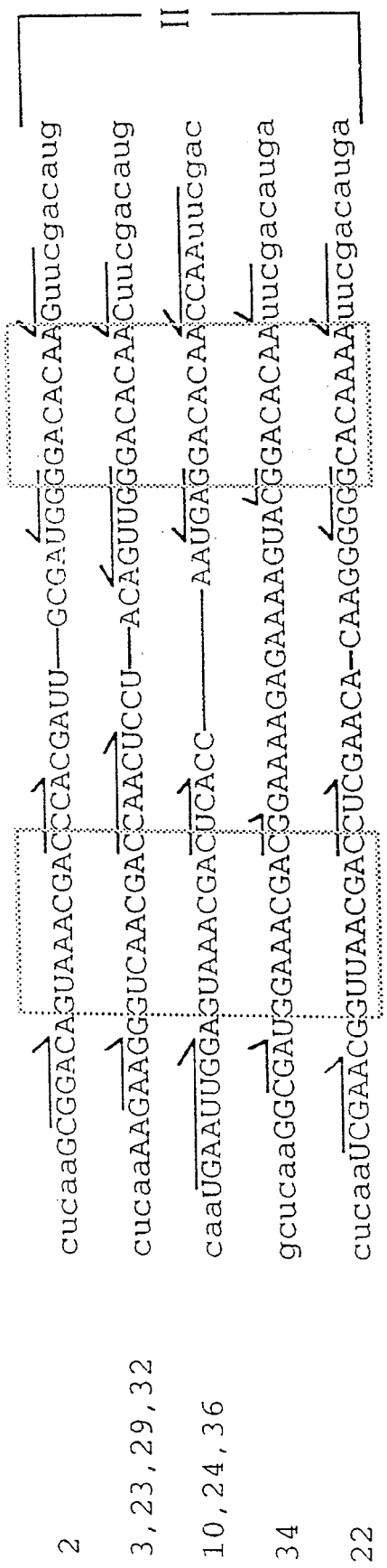
FIG. 2 lists the sequences of ligands isolated by the present invention as nucleic acid ligands to the HIV-1 tat protein (SEQ ID NO:4–19). The sequences are grouped according to common secondary structures and primary sequence in three motifs (I, II, and III). Inverted repeat sequences that predict RNA helices are shown with arrows. The regions of primary sequence homology within each motif are outlined with dashed boxes. The boundaries of the sequence information essential for high affinity binding is indicated by a solid-lined box. Sequences 1 and 17 do not fit into any of the three identified motifs.

SELEX delivers high affinity ligands of a target molecule. This represents a singular achievement that is unprecedented in the field of nucleic acids research. The present invention applies the SELEX procedure to a specific target, the HIV-1 tat protein. In the Example section below, the experimental parameters used to isolate and identify the nucleic acid ligand solution to the HIV-1 tat protein are described. FIG. 2 lists the nucleic acids that were sequenced after 10 iterations of the SELEX process.

FIG. 1 shows the naturally occurring TAR sequence that has been found to be a natural ligand to the tat protein. The specific site of interaction between the tat protein and the TAR sequence has been determined, and is also identified in FIG. 1.

The sequences presented in FIG. 2 are grouped into three "motifs". Each of these motifs represents a nucleic acid ligand solution to the HIV-1 tat protein. Regions of primary sequence conservation within each motif are boxed with dashed lines. Motifs I and II contain a common structure that places conserved sequences (those sequences found in all or most all of the nucleic acid sequences that make up the given motif) in a bulge flanked by helical elements. The primary sequence conservation—which is mainly in the single stranded domains of each bulge—are also similar between motifs I and II. The third motif (III) is characterized by a large loop. The three motifs are depicted schematically in FIG. 3. There is no apparent similarity between the nucleic acid ligands identified herein and the TAR sequence given in FIG. 1.

A boundary analysis determination was performed on one of the ligand sequences in motif III. The boundaries of recognition are indicated by a solid-lined box in FIG. 2. The boundary determination was performed according to previously described techniques. See, Tuerk et al. (1990) J. Mol. Biol. 213:749–761; Tuerk et al. (1990) Science 249:505–510.

Figure 4:
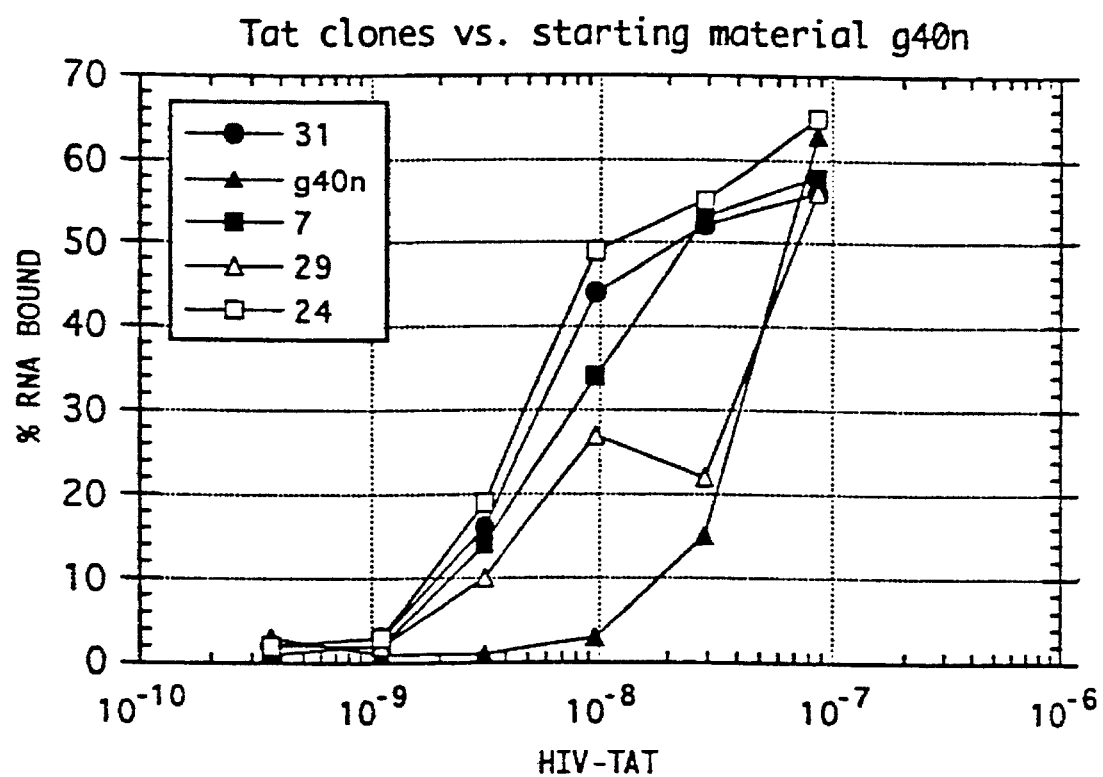
FIG. 4 is the tat protein concentration-dependent binding of selected ligand RNAs from FIG. 2, and the 40n RNA candidate mixture, to nitrocellulose filters.

In FIG. 4, the binding affinities of sequences 7 (motif I), 24 (motif II), 29 (motif II), 31 (motif III) and the original candidate mixture are depicted. As can be seen, members from each of the nucleic acid ligand solution motifs have increased affinity to the tat protein relative to the candidate mixture of nucleic acids. Each of the ligands exhibits a significantly greater affinity to the tat protein relative to the TAR sequence.

In order to produce nucleic acids desirable for use as a pharmaceutical, it is preferred that the nucleic acid ligand 1) binds to the target in a manner capable of achieving the desired effect on the target; 2) be as small as possible to obtain the desired effect; 3) be as stable as possible; and 4) be a specific ligand to the chosen target. In most, if not all, situations it is preferred that the nucleic acid ligand have the highest possible affinity to the target.

In copending and commonly assigned U.S. Pat. application Ser. No. 07/964,624, methods are described for obtaining improved nucleic acid ligands after SELEX has been performed. This application, entitled Methods of Producing Nucleic Acid Ligands is specifically incorporated herein by reference. Included in this application are the following methods relating to: Assays of ligand effects on target molecules; Affinity assays of the ligands; Information boundaries determination; Quantitative and qualitative assessment of individual nucleotide contributions to affinity via secondary SELEX, nucleotide substitution, and chemical modification experiments; and structural determination. The present invention includes improvements to the nucleic acid ligand solution derived according to these procedures.

Figure 3A:
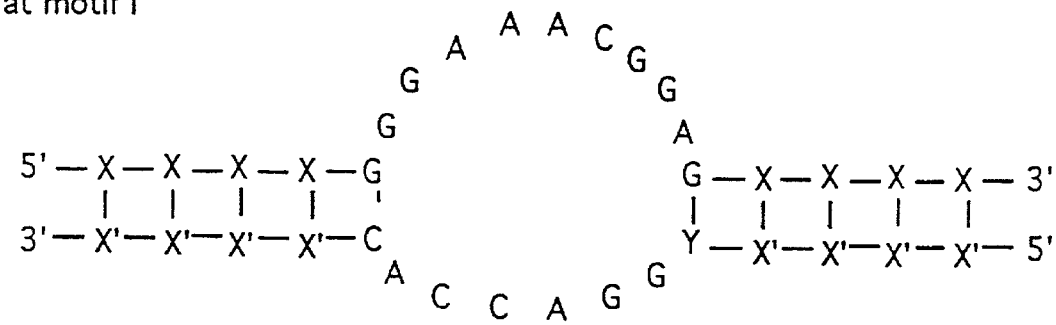
FIG. 3 depicts a schematic diagram of the consensus secondary structure and primary sequence of each of the ligand motifs given in FIG. 2 (SEQ ID NO:4–19). X indicates non-conserved nucleotide positions. X' indicates a base-pairing complement to X at that position in a helix, R indicates purine and Y pyrimidine. The dashed line in motif III indicates a variable number of nucleotides at that portion of the loop.
Figure 3B:
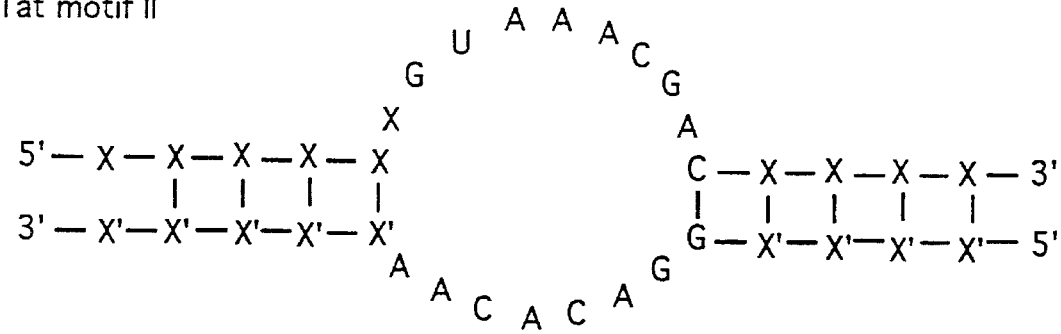
Figure 3C:
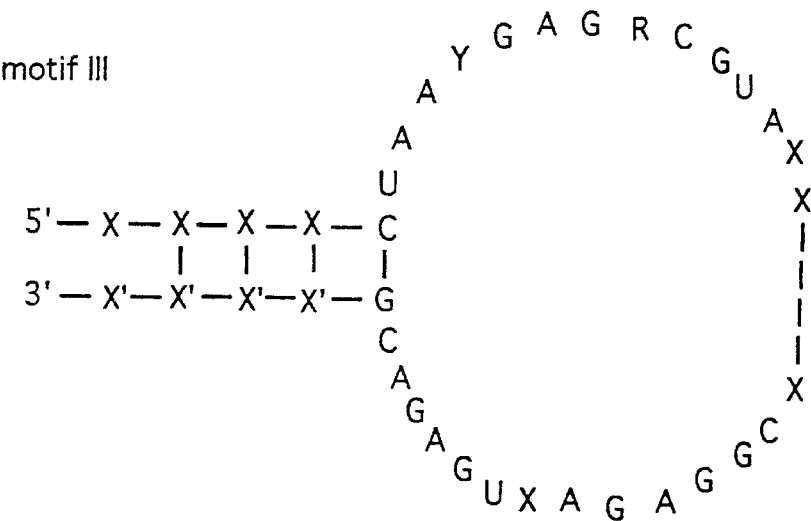

This invention includes the specific nucleic acid ligands shown in FIG. 2 and the nucleic acid ligand solutions as depicted schematically in FIG. 3. The scope of the ligands covered by this invention extends to all ligands to the tat protein identified according to the SELEX procedure. More specifically, this invention includes nucleic acid sequences that are 1) substantially homologous to and that have substantially the same ability to bind the tat protein as the specific nucleic acid ligands shown in FIG. 2 or that are 2) substantially homologous and that have substantially the same ability to bind the tat protein as the nucleic acid ligand solutions shown in FIG. 3. By substantially homologous, it is meant, a degree of primary sequence homology in excess of 70% most preferably in excess of 80%. Substantially the same ability to bind the tat protein means that the affinity is within two orders of magnitude of the affinity of the substantially homologous sequence described herein. It is well within the skill of those of ordinary skill in the art to determine whether a given sequence—substantially homologous to those specifically described herein—has substantially the same ability to bind the tat protein.

A review of motifs I, II and III, and the binding curves shown in FIG. 4, show that sequences that have little or no primary sequence homology may still have substantially the same ability to bind the tat protein. If one assumes that each of these motifs of ligands binds the same binding site of the tat protein, it is clear that binding is controlled by the secondary or tertiary structure of the nucleic acid ligand. Certain primary structures—represented by motifs I, II and III herein—are apparently able to assume structures that appear very similar to the binding site of the tat protein. For these reasons, the present application also includes nucleic acid ligands that have substantially the same structural form as the ligands presented herein and that have substantially the same ability to bind the tat protein as the nucleic acid ligands shown in FIG. 2 or FIG. 3. Wherein substantially the same structure includes all nucleic acid ligands having the common structural elements of motifs I, II and III that lead to the affinity to the tat protein.

This invention also includes the ligands as described above, wherein certain chemical modifications have been made in order to increase the in vivo stability of the ligand or to enhance or mediate the delivery of the ligand. Examples of such modifications include chemical substitutions at the ribose and/or phosphate and/or base positions of a given RNA sequence. See, e.g., Cook et al. PCT Application WO 9203568; U.S. Pat. No. 5,118,672 of Schinazi et al.; Hobbs et al. Biochem. 12:5138 (1973); Guschlbauer et al. Nucleic Acids. Res. 4:1933 (1977); Schibaharu et al. Nucl. Acids. Res. 15:4403 (1987); Pieken et al. Science 253:314 (1991).

The nucleic acid ligands and nucleic acid ligand solutions to the HIV-1 tat protein described herein are useful as pharmaceuticals and as part of gene therapy treatments. According to methods known to those skilled in the art, the nucleic acid ligands may be introduced intracellularly into cells infected with the HIV virus, where the nucleic acid ligand will compete with the TAR sequence for the tat protein. As such, transcription of HIV genes can be prevented.

EXAMPLE: SELEX on HIV-1 tat Protein.

tat protein was purchased from American Bio-Technologies, Inc. Templates for in vitro transcription were produced by PCR using the following oligonucleotides:

| | |
|---|---|
| 5'-CCGAAGCTTAATACGACTCACTATAGGGAGCTCAGAATAAACGCTCAA-3'<br>(5' primer) | (SEQ ID NO: 1) |
| 5'-GCCGGATCCGGGCCTCATGTCGAA-[40n]-TTGAGCGTTTATTCTGAGCTCCC-3'<br>(variable template) | (SEQ ID NO: 2) |
| 5'-GCCGGATCCGGGCCTCATGTCGAA-3'<br>(3' primer) | (SEQ ID NO: 3) |

SELEX rounds were conducted as described in Tuerk et al., (1992) Proc. Natl. Acad. Sci. USA, in press, and in the SELEX Applications, under the following conditions: Binding reactions were done with 13 nanomolar tat protein and 1.3 micromolar RNA in a volume of 2 mls for rounds 1 and 2, and 6.5 nanomolar tat protein and 0.65 micromolar RNA in 4 mls for rounds 3–10.

RNA synthesis. In vitro transcription with oligonucleotide templates was conducted as described by Milligan et al. (1987) Nucl. Acid. Res. 15:8783–8798. All synthetic nucleic acids were made on the Applied Biosystems model 394-08 DNA/RNA synthesizer using standard protocols. Deoxyribonucleotide phosphoramidites and DNA synthesis solvents and reagents were purchased from Applied Biosystems.

Affinity assays with labeled RNA and HIV-1 tat protein. Model RNAs for refinement of the 5' and 3' boundaries and for determination of the effect of substitutions were labeled during transcription with T7 RNA polymerase as described in the SELEX Applications, except that $\alpha$-$^{32}$P-ATP was used, in reactions of 0.5 mM C, G, and UTP with 0.05 mM ATP. All RNA-protein binding reactions were done in a "binding buffer" of 200 mM KOAc, 50 mM Tris-Hcl pH 7.7, 10 mM dithiothreitol. RNA and protein dilutions were mixed and stored on ice for 30 minutes then transferred to 37° C. for 5 minutes. In binding assays the reaction volume was 60 ul of which 50 ul was assayed. Each reaction was suctioned through a pre-wet (with binding buffer) nitrocellulose filter and rinsed with 3 mls of binding buffer after which it was dried and counted for assays or subjected to elution and assayed for chemical modification. In comparisons of binding affinity, results were plotted and the protein concentration at which half-maximal binding occurred (the approximate Kd in conditions of protein excess) was determined graphically. The results of the binding assays are given in FIG. 4.

---

We claim:

1. A nucleic acid ligand to the HIV-1 tat protein produced according to a method comprising:
   a) preparing a candidate mixture of nucleic acids;
   b) contacting the candidate mixture with the HIV-1 tat protein, wherein nucleic acids having an increased affinity to the HIV-1 tat protein relative to the candidate mixture may be partitioned from the remainder of the candidate mixture;
   c) partitioning the increased affinity nucleic acids from the remainder of the candidate mixture; and
   d) amplifying the increased affinity nucleic acids to yield a mixture of nucleic acids enriched for nucleic acids an increased affinity to the protein; whereby nucleic acid ligands of the HIV-1 tat protein are produced.

2. The nucleic acid ligand of claim 1 being a single stranded nucleic acid.

3. The nucleic acid ligand of claim 1 being a single stranded RNA.

4. A purified and isolated non-naturally occurring nucleic acid ligand to the HIV-1 tat protein.

5. The nucleic acid ligand of claim 4 wherein said ligand is selected from the group consisting of the sequences set forth in FIG. 2.

6. The nucleic acid ligand of claim 4 wherein said ligand is selected from the group consisting of: motif I (SEQ ID NOS.:4–10), motif II (SEQ ID NOS.:11–15), and motif III (SEQ ID NOS.:16–17), as shown in FIG. 3, wherein X is a non-conserved nucleotide position, X' is a base-pairing complement to X at that position in a helix, R is a purine and Y is a pyrimidine.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CCGAAGCTTA ATACGACTCA CTATAGGGAG CTCAGAATAA ACGCTCAA        48

( 2 ) INFORMATION FOR SEQ ID NO:2:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCCGGATCCG GGCCTCATGT CGAANNNNN NNNNNNNNN NNNNNNNNN NNNNNNNNN        60

NNNNTTGAGC GTTTATTCTG AGCTCCC        87

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCCGGATCCG GGCCTCATGT CGAA        24

( 2 ) INFORMATION FOR SEQ ID NO:4:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

AAGCCUCAGU AAGGCAACGG AAUCCGCAAG AGGAUGGACC ACUUCGACAU G        51

( 2 ) INFORMATION FOR SEQ ID NO:5:

( i ) SEQUENCE CHARACTERISTICS:
    ( A ) LENGTH: 55 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

GCUCAACACG AAGGAAACGG AGGGAAUCUU GAAGAACCCG GACCACUUCG ACAUG     55

( 2 ) INFORMATION FOR SEQ ID NO:6:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

CUCAAGCGGA AUGGAAACGG AGCCAUCAAC AAGCUGGCGG ACCACAUUCG ACAU     54

( 2 ) INFORMATION FOR SEQ ID NO:7:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

UCAACAAACG AAGGAAACGG AUGACCCAAG CAGGUCAGGA CCACUUCGAC AUG     53

( 2 ) INFORMATION FOR SEQ ID NO:8:

( i ) SEQUENCE CHARACTERISTICS:
    ( A ) LENGTH: 56 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

CGCUCAAACG AAGGAAACGG AUGCGGACAU AUGUGCCGCA GGACCACUUC GACAUG     56

( 2 ) INFORMATION FOR SEQ ID NO:9:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:9:

AAACACAUCG AAGGUAACGG AGCGAAAAGA ACGCGGACCA CUUCGACAUG     50

( 2 ) INFORMATION FOR SEQ ID NO:10:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

AACGCUCAAG CGGGCAACGG AGUCCUGAAC GGACGGACCA CCGCAAGAAU     50

( 2 ) INFORMATION FOR SEQ ID NO:11:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

CUCAAGCGGA CAGUAAACGA CCCACGAUUG CGAUGGGAC ACAAGUUCGA CAUG　　54

( 2 ) INFORMATION FOR SEQ ID NO:12:

( i ) SEQUENCE CHARACTERISTICS:
　　　　( A ) LENGTH: 54 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:12:

CUCAAAAGAA GGGUCAACGA CCAACUCCUA CAGUUGGGAC ACAACUUCGA CAUG　　54

( 2 ) INFORMATION FOR SEQ ID NO:13:

( i ) SEQUENCE CHARACTERISTICS:
　　　　( A ) LENGTH: 49 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:13:

CAAUGAAUUG GAGUAAACGA CUCACCAAUG AGGACACAAC CAAUUCGAC　　49

( 2 ) INFORMATION FOR SEQ ID NO:14:

( i ) SEQUENCE CHARACTERISTICS:
　　　　( A ) LENGTH: 56 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:14:

GCUCAAGGCG AUGGAAACGA CGGAAAAGAG AAAAGUACGG ACACAAUUCG ACAUGA　　56

( 2 ) INFORMATION FOR SEQ ID NO:15:

( i ) SEQUENCE CHARACTERISTICS:
　　　　( A ) LENGTH: 55 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:15:

CUCAAUCGAA CGGUUAACGA CCUCGAACAC AAGGGGGGCA CAAAAUUCGA CAUGA　　55

( 2 ) INFORMATION FOR SEQ ID NO:16:

( i ) SEQUENCE CHARACTERISTICS:
　　　　( A ) LENGTH: 55 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:16:

AAGAGAAUCU AACGAGACGU AAGCCGUCGG AGAAUGAGAC GAUUCGACAU GAGGC　　55

( 2 ) INFORMATION FOR SEQ ID NO:17:

( i ) SEQUENCE CHARACTERISTICS:

(A) LENGTH: 53 base pairs
(B) TYPE: nucleic acid
(C) STRANDEDNESS: single
(D) TOPOLOGY: linear (xi) SEQUENCE DESCRIPTION: SEQ ID NO:17:

AGUGAGGACU AAUGAGGCGU ACGACCGGAG AUUGAGACGU CUUCGACAUG AGG    53

(2) INFORMATION FOR SEQ ID NO:18:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:18:

CGCUCAAGGC GACGGGACUG CAAGCAUGGA GCUAACGAGA AAAUUGCUUC GACA    54

(2) INFORMATION FOR SEQ ID NO:19:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:19:

CGCUCAACCU GGAGAGGAUC GCUGGCGGGC UUGAUCCCCA GAUCAAAUUC GACA    54

(2) INFORMATION FOR SEQ ID NO:20:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:20:

CCAGAUCUGA GCCUGGGAGC UCUCUGG    27